United States Patent [19]

de la Torre

[11] Patent Number: 4,728,511
[45] Date of Patent: Mar. 1, 1988

[54] COMPOSITION AND METHOD FOR THE TREATMENT OF CANCER

[76] Inventor: Daniel M. de la Torre, Isabel la Catolica No. 271, Colonia Obrera, Mexico 8, D.F., Mexico

[21] Appl. No.: 863,804

[22] Filed: May 12, 1986

Related U.S. Application Data

[60] Continuation of Ser. No. 723,986, Apr. 16, 1985, abandoned, which is a continuation of Ser. No. 360,541, Mar. 22, 1982, abandoned, which is a division of Ser. No. 145,419, May 1, 1980, abandoned.

[51] Int. Cl.$^4$ .................. A61K 35/36; A61K 33/06
[52] U.S. Cl. ................................. 424/95; 424/154; 514/885; 514/937
[58] Field of Search .................. 424/95, 154; 518/937, 518/885

[56] References Cited

PUBLICATIONS

Chem. Abst., 34:5522, 1940.
Chem. Abst., 52:8256b, 1958.
Dyer, An Index of Tumor Chemoth., Mar. 1949, pp. 10, 11 & 140.

Primary Examiner—J. R. Brown
Assistant Examiner—John W. Rollins, Jr.
Attorney, Agent, or Firm—Sughrue, Mion, Zinn, Macpeak and Seas

[57] ABSTRACT

A composition useful for the treatment of cancer comprises a colloidal or semi-colloidal suspension of DNA-repressor proteins derived from a finely divided mammal nerve tissue, particularly brain tissue.

A method of treating cancer comprises administering to the patient a suitable daily dosage of the above composition, accompanied by the administration of suitable doses of immuno globulin (gamma-globulin), during a period of from 45 to 60 days.

7 Claims, No Drawings

COMPOSITION AND METHOD FOR THE TREATMENT OF CANCER

This is a continuation of application Ser. No. 723,986, filed 4/16/85, which is a continuation of application Ser. No. 360,541 filed 3/22/82, which is a division of Ser. No. 145,419, filed 5/1/80, all abandoned.

FIELD OF THE INVENTION

The present invention refers to the treatment of cancer and, more particularly, it is related to a composition and a method of treating cancer, useful for involuting a carcinoma in any stage of evolution thereof.

BACKGROUND OF THE INVENTION

It has been fully recognized in recent years that cancer can start in just one of the body's billions of cells, triggered by a stray of radiation, a trace of toxic chemical, a virus or a random error in the transcription of the cell's genetic message. Once the genetic message of the cell has been altered by any external or internal influence, the cell start to divide to form other abnormal cells, under a process that violates normal genetic restraints. The immune system of the body, on the other hand, which is normally alert to the presence of any type of alien cells, fails to respond properly and its defense units refrain from attacking and destroying the intruder cells. Unlike healthy cells, which stop reproducing after repairing damage or contributing to normal growth, the aberrant cells (cancerous cells) have no boundary in connection with the division properties and continue to proliferate widly, forming a growing mass or tumor that expands into healthy tissue and competes with normal cells for nutrition. Also, the malevolent cells may be transferred into the bloodstream or the lymphatic system which carries them all over the body thus creating what is termed metastasis.

While workers in the art usually have the strong feeling that cancer could be stopped if the altered genetic message of the cell could be restored, no means have been deviced up to the present date to effect such restoration. Therefore, the customary and what are considered the best treatments for cancer is to have the lifes of the patients prolonged for a few years by one or a combination of three kinds of often unpleasant, debilitating and sometimes disfiguring treatment, namely, surgery, radiation and chemotherapy. Regardless of the existence of these types of treatments commonly applied to cancerous patients, two-thirds of all cancer victims eventually die of the disease.

In more recent years some further and more remarkable developments have been made through the production of a relatively efficient vaccine for treating human cancer in breast, lungs, ovaries, cervix and gastrointestinal tract, said vaccine being prepared from a tumor material derived from at least one or more human cancers developing in a specific predetermined organ and admixing several of said materials and treating the same to produce vaccines which are relatively effective against the development of cancer in the above mentioned organs of the human body. However, the percentage of relief obtained by the patients is relatively low and the production of said vaccine is expensive and painstaking, whereby this may be considered at most as a partial cure and as one of the best efforts made in the recent times towards the alleviation of this affliction.

One other most hopeful discovery made in recent years is interferon (IF) which seems to be a protein contained and produced in minute amount by living cells, but while the alleviation of the disease through the use of interferon seems to be very promising, the obstacles encountered in the development of production of said substance are almost impossible to overcome, because interferon is a very specific substance which is produced by animals and which acts only in animals of the same species and is not of general application. In other words, interferon produced by human cells is only effective against cancer of humans, whereas interferon produced by other types of mammals or vertebrate animals are specific only in the same species of the animals whose cells produce said interferon, whereby there is no possibility of obtaining animal interferon to be used in humans or viceversa. Therefore, the only manner of having an interferon which may be active against human cancer is to obtain said interferon from human cells and this, obviously, represents an almost unbeatable obstacle in view of the tremendously high cost and the exaggerately small amounts in which interferon may be produced, whereby this technique may not be the best solution for cancer disease which, only in the United States of Americal kills around half a million people every year.

Therefore, regardless of the tremendous efforts and expenses made by worldwide institutions endeavored in the research of cancer disease, up to the present date no reasonable cure has been developed which may be regarded as specific or at least reasonably effective against many kinds of cancer. Therefore, the only way of attacking cancer and this only in certain instances such as in melanoma and certain adenocarcinomas of the mammal gland, is to discover the cancer in an early stage of development and to apply surgery and thereafter radiation and chemotherapy to try to cure the disease, with a low percentage of satisfactory cases.

BRIEF SUMMARY OF THE INVENTION

Having in mind the defects of the prior types of cure for cancer disease, it is an object to the present invention to provide a composition for the treatment of cancer which is useful for most types of cancer and which may be effective in any stage of development of the disease.

It is another object of the present invention to provide a composition for the treatment of cancer, which will directly act upon the genetic message of the cells in order to inhibit the wide reproduction abilities of cancerous cells.

One other and more particular object of the present invention is to provide a composition for the treatment of cancer which is derived from an abundant starting material available in vast amounts.

It is another object of the present invention to provide a method of treating cancer in any stage of development of said disease.

The foregoing object and others ancillary thereto are preferably accomplished as follows:

According to a preferred embodiment of the present invention, cancer is treated at any stage of development of the disease by the method which comprises administering to the patient through the oral route, a suitable daily dosage, during a period of time of about from 45 to 60 days, of a composition comprising a colloidal or semi-colloidal suspension of DNA-repressor proteins derived from a fresh mammal nerve tissue, particularly brain tissue, alternated with the parenteral adminstration of immunoglobulin gamma globulin).

The novel features that are considered characteristics of the present invention are set forth with particularly in the appended claims. The invention itself, however, both as to its organization and its method of operation, together with certain theoretical considerations to which applicant does not wish to be bound, as well as additional objects and advantages thereof, will best be understood from the following detailed description of certain specific embodiments which are merely given as illustrative but not as limitative of the present invention.

DETAILED DESCRIPTION

In recent years it has been learned that a fundamental property of living cells is their ability to turn their genes on and off in response to extracellular signals. In the human body, for example, every cell (with the exception of a few cell types such as the red blood cell) has the same set of genes, yet in the course of embryonic development cells take on different shapes and functions as their genes are selectively switched on and off.

Through the study of gene regulation in bacteria and viruses it has been learned in recent years that a fundamental mechanism of gene control depends on the interaction of protein molecules with specific regions on the long-chain molecule of DNA. As a result of this interaction genes are switched on or off. In the best-understood instances genes are switched off by controlling molecules named repressors. The existence of repressors was first hypothesized in 1960 by Francois Jacob and Jacques Monod of the Pasteur Institute in Paris. Sever years later Walter Gilbert (in collaboration with Benno Muller-Hill and, Ptashne, working independently at Harvard University, succeeded in isolating repressors from bacteria (see "Genetic Repressors," by Mark Ptashne and Walter Gilbert; Scientific American, June 1970). Later it was shown that repressors could bind tightly and specifically to sites on DNA called operators and that in so doing they could prevent genes adjacent to the operators from being transcribed and translated into proteins.

In man, as in bacteria, a gene can be defined as a sequence of bases along a DNA molecule. The DNA molecule consists of two long chains of nucleotides wound in a double helix and linked to each other by hydrogen bonds. Each nucleotide consists of a deoxyribose sugar, a phosphate group and one of four nitrogenous bases: adenine, guanine, thymine or cytosine (abbreviated A, G, T and C). The sugar and phosphate groups form the backbone of each chain; the bases extend toward the central axis of the double helix and pair with the bases extending from the other chain. The sequences of bases along the chain are complementary: A always pairs with T and G always pairs with C. The information content of DNA is specified by the sequence of bases. A typical gene consists of roughly 1,000 base pairs.

The translation from gene to protein begins with the enzyme RNA polymerase, which copies the base sequence into a complementary sequence on the linear molecule of "messenger" RNA. The intracellular translating machines called ribsomes attach themselves to the messenger RNA and translate its base sequence into a sequence of amino acids, which are linked to form a protein molecule.

It is clear that the translation of a gene into a protein molecule might conceivably be repressed or blocked at any one of several stages along the complex gene. Recent studies have determined that repression takes place directly at the DNA molecule, so that the genetic information is not transcribed into "messenger" RNA unless the repressor is inactivated.

Repressors are generally small sized acid proteins generated by a so called regulator gene in the DNA, which attach themselves to the promoter region of the operator of a gene thus preventing the RNA polymerase to attach itself to said promoter region and assemble the messenger RNA.

Once having reviewed the basic mechanism of repression of the transcription of the gene, and while applicant does not wish to be bound to any theoretical explanation of the manner of acting of the composition of the present invention, it is to be stated that it is believed that cancer is the chemical alteration of the order of the nucleotides adenine, guanine, thymine and cytosine constituting the gene which regulates cellular duplication and codifies the synthesis of a specific protein which works as a repressor of an operator gene. This alternation, caused by physical, chemical or biological agents in a cell, transmits hereditarily this transformation to the daughter cells which cannot appropriately synthesize the repressor, thereby generating the wide reproduction of the cell and forming the abnormal tissue masses (primary tumors) which may disseminate through metatasis to other organs.

In a normal cell the specific repressor protein adheres to the DNA, as mentioned above, in the promoter region of a gene operator and inhibits transcription of the structural genes that control the development and the synthesis of RNA.

On the other hand, there are certain specific receptor proteins located at the cythoplasm of the cell, adhered to the membrane and which are sensitive to the intercellular contact and record the empty spaces of a tissue, probably through electromagnetic changes, thereby inducing cellular duplication when they migrate towards the nucleus of the cell and adhere to the DNA, particularly to the regulator gene and avoid synthesis of the repressor protein which controls the population of cells in a living organism.

It is believed that the cancerous cell contains an altered repressor protein which does not work or is merely deprived of said protein, depending on the change which has been caused in the regulator gene and, therefore, said cell is always in a condition of continuous transcription of the structural genes, thus resulting in an indefinite duplication.

The susceptibility of a cell towards cancer very much depends on an increase in the permeability of its membrane which permits physical, chemical or biological cancer developing agents to enter into contact with its DNA. Thus, some hormones act by affecting the speed of enzymatic catalysis or by altering the permeability of the cellular membrane and this circumstance renders those tissues which are subject to a continuous hormonal stimulus more prone to cancer, for instance, the mammarian gland and the uterus.

Lack of nutrition may be another circumstance causing an increase in the permeability of the cellular membrane, as well as the depression of the immuno competence, which are factors facilitating the action of oncogenic viruses.

It has also been ascertained that the cytoplasm of every cell in a living tissue, contains a multiplicity of molecules of a so called receptor protein. This protein, probably due to electromagnetic or electrochemical changes, senses the empty spaces of the neighboring tissue where cells are needed and, upon doing so, the receptor protein migrates toward the nucleus of the cell, attaching to the regulator gene of the DNA which therefore will no longer produce the repressor protein to block the promoter region of the operator gene. Therefore, said promoter region will cease to be repressed and will trigger the operator gene to start the formation of messenger RNA and the reproduction of the cell to fill the empty spaces of the tissue. The action will be reversed when the receptor proteins sense no empty space once it is filled with new cells. This may be the mechanism by which a predetermined cell reproduces itself only when needed and remains dormant in this respect when reproduction is not needed by the living organism.

The increase in the permeability of the membrane of a cell, may permit external oncogenic agents, mainly viral DNA, to permeate said membrane and migrate to the nucleus of the cell, attaching itself to the regulator gene permanently, whereby said regulator gene will no longer produce the appropriate repressor protein. Therefore, the continuous reproduction of the cell will be triggered by the absence of the repressor protein and the cell will become malignant.

It is clear, therefore, that if a repressor protein contained in a tissue is administered to a patient, said repressor protein will substitute the repressor protein no longer being produced by the malignant cell, and will act directly on the promoter region of the operator gene to prevent the latter to trigger the continuous reproduction of said cell.

It has been found that all nervous tissue of mammals, in being cells that never reproduce during the life time of the individual, contain high amounts of these repressor proteins, whereby when administered to a patient through the gastrointestinal tract, are transported through the lymphatic and blood systems to the cells affected by cancer. As these cells have the permeability of their membranes considerably increased, the administered repressor protein will penetrate said membranes and attach to the promoter region of the operator gene of the DNA of said cells, acting as repressor molecules instead of the normal repressor molecules that are not being produced by the regulator gene of the malignant cell.

That is the reason why a composition of matter containing a colloidal or semi-colloidal suspension of DNA repressor proteins derived from a fresh mammal nerve tissue and particularly from brain tissue, has been found to be extremely active in repressing and preventing reproduction of cancerous cells and ultimately produce the involution and disappearance of the tumors originally formed by said cells.

This type of repressor proteins provided by the composition of the present invention not only act within the tumor itself but also act through the chyliferous vessels and the blood vessels in order to attack metastasized cells, thereby also inhibiting metastasis of cancer in a patient affected by said ailment.

The composition of nervous tissue in accordance with the present invention may be prepared by immersing a nervous fresh animal tissue obtained from a recently slaughtered mammal into an aqueous solution of iodine (1:2500) during a period of time of from about 1 to 3 minutes, in order to sterilize said tissue and to avoid the participation of any living bacteria or other germs.

The fresh tissue is removed from the iodine solution and is throughly washed with distilled water in order to wash the absorbed iodine and thereafter the said tissue is comminuted, for instance, in a blendor, during a period of 1 minute or less, in order to form a colloidal or semicolloidal mass which is preseved under freeze conditions, because the pharmacological action very much depends on the integrity of the proteins that it contains, which proteins are sensitive to high temperatures.

In order to administer the composition of matter of the instant application, the same is thawn and applied orally to the patient suffering of cancer, preferably at dosage of from 0.5 to 20 mg/mg of tumoral tissue determined in the patient and for a period of time of from about 45 to 60 days, whereafter a remarkable involution of the disease is observed in a large proportion of the cases.

The following examples will illustrate the effectiveness of the compositions of the present invention as applied by the method of treating cancer disease described above.

EXAMPLE 1

A group of 20 hamsters was injected with cancerous cells to induce an adenocarcinoma in the mammarian gland and the cancer was allowed to develop to an intermediate stage. When the adenocarcinon a was fully developed in all of the twenty selected hamsters, a group of ten of said hamsters was treated with a compositions comprising finely divided and sterilized brain tissue of a recently slaughtered bovine animal, in dosages of 1 ml each 24 hours during 30 days, equivalent to a dose of about 6 mg/kg of hamster per day. No immuno-globulin(gamma-globulin) was used in the treatment of the hamsters.

The group of ten hamsters selected for treatment was closely observed and by the end of the 15th day as of initiating the treatment, the tumoral tissues began to decrease and involute, whereas after 30 days of treatment a complete disapperance of the adenocarcinoma was accomplished, and the weight of the animals increased 7%, said hamsters being fully recovered by the end of the 30th day.

The group of ten hamsters which were not treated in accordance with the above, were also observed. All of them, without a single exception, showed a considerable increase in the tumoral volumes, loss of living characteristics and loss of weight of up to about 20%. All of said hamsters died within the next 90 days.

EXAMPLE 2

The procedure of Example 1 was repeated, but using a brain tissue obtained from a recently slaughtered equine animal. The results proved to be the same as in Example 1.

EXAMPLE 3

A group of 30 voluntary human patients suffering of fully developed and metasasized cancer in different organs was treated with a composition prepared as follows: A portion of brain tissue obtained from a recently slaughtered bovine animal (lamb) was infused in a solution of iodine (1:2500) during two minutes, the disinfected tissue was throughly washed with distilled water and thereafter it was comminuted in a waring blendor during a period of 1 minute to reduce the tissue to the consistency of a heavy syrup.

The thirty selected patients were distributed as follows: twelve of said patients had received one chemotherapy treatment by the administration of vincristine, adreamicine and cyclophosphamide; fifteen other patients had been already treated two or three times with chemotherapy and several times with radiotherapy, and a further group of three patents was already treated by a multiplicity of chemotherapy sessions and radiotherapy and had a very advanced cancer attacking vital organs, such as liver, lungs, kidney and intestine.

All the thirty patients were treated by administering an approximate daily dosage of 1 mg/mg of tumoral tissue (determined for each patient) of the above composition, and were also administered with either human immuno-globulin (gamma-globulin) at a cosis of 1 ml each 72 hours parenterally during three weeks, or immunogolbulin (gamma-globulin) obtained from horse in the form of suppositories of 10 mg, by administering one suppository every 24 hours during 12 days, as a means to protect the patients against viral reinfections.

Also, all the patients were administered calcium phosphate pills of 400 mg each, three times per day during the period of administration of the gamma-globulin.

The results obtained with the above treatment are as follows: The twelve patients that had received only one single chemotherapy treatment had a perfect evolution, with complete dissaperance of the tumoral tissues and, after one year of control as of finalization of the treatment, the turmoral tissue indicators, namely, latic dehydrogenase and alkaline phosphatase, came down to normal values of about 193 International Units (IU) for the latic dehydrogenase and of about 72 IU for the alkaline phosphatase. None of said twelve patients have shown any tendency towards an increase in the above indicators during the one year of control closely kept upon them.

The fifteen patients that had suffered already two or three treatments by chemotherapy and several radiotherapy treatments, did not respond satisfactorily to the treatment and, while in some cases the carcinomas were reduced in volume, the treatment did not relieve them fully from the disease. These patients had to continue with chemotherapy and radiotherapy treatments after the above mentioned treatment, without any satisfactory results.

The three patients who had received many chemotherapy treatments and radiotherapy treatments and that had a cancer affecting vital organs, all of them died despite of the treatment of the present invention.

The above shows that the treatment is more effective when the cancer has not been treated by chemotherapy or radiotherapy, regardless of the stage of development (under reasonable limits) and metastasis involved, and that the said chemotherapy treatments, by reducing the immunological response of the patients, renders them more prone to viral infections, and it is believed that the viral infections have much influence in the development of cancer by modification of the genetic message of the cells of the patients. Out of the thirty cases, only twelve were satisfactorily treated and are fully alleviated from the disease, which means that the treatment carried out as described in this example has proven to be effective in at least 40% of the cases, by using the brain tissue of a bovine animal.

EXAMPLE 4

Another group of twenty voluntary patients, 10 of which had not received more than one chemotherapy treatment and no radiotherapy treatment at all, and 10 of which had received several such treatments (chemotherapy and radiotherapy) were also treated by using the same type of treatment described in example 3 above, but by preparing the composition of the present invention using brain tissue obtained from primate animals, particularly American monkey, with the result that nineteen out of the twenty cases were completely alleviated from the disease and the controls exerted upon said patients during one year as of treatment have kept the tumoral tissue indicators within normal levels, which means that said patients have been fully alleviated from cancer disease and only one had to undergo a repeated treatment because the involution of the tumoral tissues, while satisfactory when the first treatment was applied, was not sufficient to completely inhibit all the cancerous cells and perhaps the viral infections affecting said patient after the treatment caused a reinstatement of the tumoral growth, whereby a second treatment identical with the above described treatment was applied to him. Said patient is under observation up to the present time, also with satisfactory but still uncertain results.

Thus, the treatment carried out in accordance with this example showed 95% favorable results.

The above examples give some hints as to the effectiveness of the composition and treatment in accordance with the present invention, in the sense that, when treating hamsters with bovine or equine brain tissue, 100% success was obtained, whereas when treating humans with certain bovine brain tissues, together with gamma-globulin and calcium phosphate treatments, only 40% of the cases was considered to be entirely satisfactory. However, the proportion of alleviation was increased considerably to about 95%, when using brain tissue of primates, which are animals closer to the human race in the zoological scale.

The above might mean that, if certain legal provisions and ethical barriers are overcome, perhaps the use of human brain tissue would achieve a 100% success, but no experiments could be made with human brain tissue particularly if it is considered that the oral ingestion thereof would be ethically rejected, and it would be necessary to effect lyophilization of said tissues in order to administer them perenterally.

However, it is a fact that the closer the animal is to the human race, the more effective is the action of the brain tissues of said animals in alleviating the development of cancer.

The above, obviously, may be due to the fact that the repressor proteins contained in the brain tissue of a species of animals close to the human race, may be more similar to the human repressors that are affected when cancerous cells are developed, thus acting as a perfect substitute for said lost or altered repressor proteins, which are no longer being produced by cancerous cells.

It may be seen from the above that for the first time a simple treatment for cancer disease has been developed and a very effective composition of matter has also been provided which may be regarded as very promising in the treatment of cancer disease, giving a percentage of successful cases which is much higher than those produced by any treatment of the prior art that has come to the attention of applicant.

Although certain specific embodiments of the present invention have been shown and described above, it is to be understood that many modifications thereof are possible. The present invention, therefore, is not to be restricted except insofar as is necessitated by the prior art and by the spirit of the appended claims.

What is claimed is:

1. A composition of matter for the treatment of adenocarcinoma in conjunction with daily dosages of gamma globulin and calcium phosphate, said composition of matter comprising an iodine sterilized colloidal or semi-colloidal suspension of finely divided brain tissue derived from a bovine, equine or primate animal in a dosage sufficient for involuting the adenocarcinoma at any stage of evolution.

2. A composition according to claim 1, wherein said brain tissue is bovine brain tissue.

3. A composition according to claim 1, wherein said brain tissue is equine brain tissue.

4. A composition according to claim 1, wherein said brain tissue is primate animal brain tissue.

5. A composition according to claim 1, wherein said sterilized colloidal or semi-colloidal suspension of brain tissue is lyophilized.

6. A composition according to claim 1, wherein said brain tissue is sterilized by immersing brain tissue of a recently slaughtered bovine, equine or primate animal in a 1:2500 aqueous solution of iodine during a period of time of from 1 to 3 minutes, and then rinsing said tissue with distilled water.

7. A composition according to claim 6, wherein said sterilization is effected prior to comminution of the brain tissue.

* * * * *